United States Patent [19]
Samuels et al.

[11] Patent Number: 6,103,930
[45] Date of Patent: *Aug. 15, 2000

[54] RECOVERY OF 2,6-NAPHTHALENE DICARBOXYLIC ACID FROM POLYESTERS

[75] Inventors: Michael Robert Samuels, Wilmington; Marion Glen Wagonner, Hockessin, both of Del.

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 09/157,277

[22] Filed: Sep. 18, 1998

Related U.S. Application Data

[60] Provisional application No. 60/060,216, Oct. 1, 1997.

[51] Int. Cl.$^7$ .......................... C07C 51/347; C07C 51/09
[52] U.S. Cl. .......................... 562/483; 528/176; 528/272; 528/298
[58] Field of Search .............. 562/483; 528/176, 528/272, 298

[56] References Cited

U.S. PATENT DOCUMENTS

| | | | |
|---|---|---|---|
| 3,629,202 | 12/1971 | Gilkey et al. | 260/75 T |
| 5,414,113 | 5/1995 | Broeker et al. | 562/413 |
| 5,473,102 | 12/1995 | Johnson et al. | 562/483 |

FOREIGN PATENT DOCUMENTS

| | | | |
|---|---|---|---|
| 0432910 | 6/1991 | European Pat. Off. | C07C 63/38 |
| 1926034 | 11/1970 | Germany | C07C 12/14 |

OTHER PUBLICATIONS

Encyclopedia of Polymer Science and Engineering, vol. 12, pp. 29–31, 34 and 35, 1988.

Ullmann's Encyclopedia of Industrial Chemistry, Fifth edition, pp. 228–239, 1992.

H. Zhang et al., Macromolecules, 28, 7622–7629, 1995.

*Primary Examiner*—Johann Richter
*Assistant Examiner*—Rosalynd Keys

[57] ABSTRACT

This invention concerns a method for recycling polyesters comprising the hydrolysis of polyesters containing repeat units derived from 2,6-naphthalene dicarboxylic acid in the presence of a carboxylic acid which gives pure 2,6-naphthalene dicarboxylic acid suitable for use as a monomer.

16 Claims, No Drawings

RECOVERY OF 2,6-NAPHTHALENE DICARBOXYLIC ACID FROM POLYESTERS

This application claims the benefit of Provisional Application No. 60/060,216, filed on Oct. 1, 1997.

FIELD OF THE INVENTION

Disclosed is a process for recycling polyesters, such as poly(ethylene 2,6-naphthalate), by hydrolyzing them at elevated temperatures in the presence of water and a carboxylic acid to give pure 2,6-naphthalene dicarboxylic acid suitable for use as a monomer.

TECHNICAL BACKGROUND

Many types of polymers may be recycled or their chemical values recovered by various means. Polyesters of various types have been hydrolyzed or reacted with alcohols to recover the various chemical units present in the polymers. The recovered compounds are then reused, often in the formation of new polyester polymer. However in order to use a compound as a monomer in a condensation polymerization, it is well known that the compound should be pure and especially be free of various types of impurities that may interfere with a commercial scale polymerization, which should be routinely reproducible. Thus especially when recycling relatively clean scrap polymer, the recycling process should preferably be simple and yield products which are pure.

U.S. Pat. No. 5,473,102 describes the hydrolysis of polymers containing various aromatic dicarboxylic acids such as terephthalic acid, isophthalic acid and 2,6-naphthalene dicarboxylic acid (N) by hydrolysis and subsequent distillation of the hydrolysis products by codistillation with steam. The hydrolysis of N containing polyesters in the presence of a carboxylic acid is not described.

U.S. Pat. No. 3,629,202 describes the treatment of polyesters with various carboxylic acids to make them resistant to hydrolysis.

H. Zhang, et al., Macromolecules, vol. 28, p. 7622–7629 (1995) describe the kinetics of the hydrolysis of poly (ethylene 2,6-naphthalate) (PEN). The presence of added carboxylic acids for the hydrolysis is not mentioned.

SUMMARY OF THE INVENTION

This invention concerns a process for the production of 2,6-naphthalene dicarboxylic acid, comprising, contacting, at a temperature of about 120° C. to about 300° C., a poly(alkylene 2,6-naphthalate), water, and an organic carboxylic acid, other than 2,6-naphthalene dicarboxylic acid, containing 2 to about 20 carbon atoms.

DETAILS OF THE INVENTION

By a poly(alkylene 2,6-naphthalate) is meant a polymer in which at least 50 mole percent of the repeat units have the formula

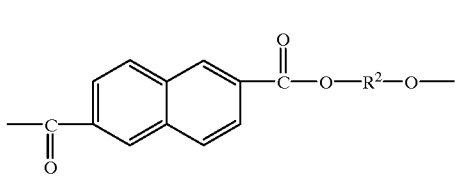

wherein $R^2$ is alkylene. In a preferred polymer all of the repeat units are (I), and in a more preferred polymer, which is PEN, $R^2$ is —$CH_2CH_2$—. The polymer of which (I) is a part may be a simple polyester, or may contain other linking groups other than polyester, such as amide or imide. It is also preferred that this polymer simply be a polyester.

The organic carboxylic acid which is present is believed to act as a catalyst for the hydrolysis reaction, and also in some way helps to provide a pure N product. It may be substituted by various functional groups which do not interfere with the hydrolysis, such as hydroxyl. Preferred organic carboxylic acids have the formula $R^3CO_2H$, wherein $R^3$ is hydrocarbyl or substituted hydrocarbyl containing 1 to 10 carbon atoms, more preferably 1 to 4 carbon atoms. It is also preferred that $R^3$ is alkyl or hydroxyl substituted alkyl. Especially preferred are acetic acid or glycolic acid. Other preferred carboxylic acids have a pKa of about 1 to about 6, preferably 2 to 5, when measured in water at a temperature of 23° C.

The amount of carboxylic acid present in the hydrolysis is not critical. For instance a useful amount is about 0.1 to about 50 volume percent of the liquid water (if present) in the process. In an optional method of determining the organic carboxylic acid present, about 0.05 to about 25 weight percent of carboxylic acid based on the weight of polyester present may be used. If the polymer contains repeat units that may yield basic materials upon hydrolysis, such as an amide linkage yielding an amine, enough carboxylic acid should be present so that free carboxylic acid is present throughout the hydrolysis.

The water may be present as liquid water or as steam or both. Preferably at least some, more preferably the major portion, of the water is present in liquid form. The amount of water needed for complete hydrolysis is at a minimum 2 moles per repeat unit (I). However it is preferred that at least 3 moles of water per mole of repeat unit (I) be present, preferably about 5 to 200 moles of water per mole of repeat unit (I).

The hydrolysis is carried out at about 120° C. to about 300° C., preferably about 150° C. to about 275° C., more preferably about 175° C. to about 250° C., and especially preferably about 210° C. to about 240° C. As is usual with most chemical reactions, the time needed to effect hydrolysis of the polymer will decrease as the temperature is raised. "Total" hydrolysis of the polymer is preferred but not necessary to obtain at least some N. However, the temperature should preferably not be so high as to cause significant decomposition of the hydrolysis products or of the organic carboxylic acid. Extensive decomposition may lead to products which contaminate the hydrolysis product(s) and may be difficult to remove.

The hydrolysis is preferably done in the substantial absence of oxygen to avoid unwanted oxidation side reactions. It may be convenient to perform the hydrolysis under an inert gas such as nitrogen. It may be advantageous to provide some agitation to accelerate the hydrolysis.

The apparatus used should be able to withstand the pressure under which the process is run, autogenous pressure or steam pressure being convenient to use. It should also be resistant to corrosion from the process ingredients at the temperatures employed. Useful materials of construction are glass (lining), stainless steel and Hastelloy® C alloy.

Once the hydrolysis is complete the slurry (assuming liquid water is present) may be cooled to reduce the autogenous pressure to atmospheric. Assuming no other solid and water insoluble products are present, the product N may be filtered off by conventional means. After washing with additional water and drying, it has been found that this product is suitable directly for use as a monomer for making polyester. Analyses indicate it is quite pure, even the polymerization catalyst residues from the hydrolyzed polyester having been separated from the N (it is assumed they are in the filtrate).

Hydrolyses run using no catalyst or other types of acid catalysts give N which is discolored or otherwise unsuitable for direct use as a monomer. In some instances, substantial amounts of polymerization catalyst residues from the hydrolyzed polyester remain in the N.

The N which is produced by the hydrolysis of the poly (alkylene 2,6-naphthalate) may be further reacted (polymerized) to form part of a condensation polymer such as a polyamide, polyester, poly(ester-amide), poly(ester-imide) or any other polymer in which ester or amide linking groups are present. Polymerization of dicarboxylic acids such as N to form polymers which are homopolymers or copolymers containing ester or amide linkages are well known. For instance, a description of the formation of isotropic polyesters may be found in B. Elvers, et al., Editors, Ullmann's Encyclopedia of Industrial Chemistry, 5th Ed., Vol. A21, VCH Verlagsgesellschaft mbH, Weinheim, 1988, p. 228–251, and H. Mark., et al., Editors, Encyclopedia of Polymer Science and Engineering, Vol. 12, John Wiley & Sons, New York, 1988, p. 1–75, while a description of the formation of thermotropic liquid crystalline polyesters, particularly aromatic polyesters, may be found in Example 2 herein, B. Elvers, et al., Editors, Ullmann's Encyclopedia of Industrial Chemistry, 5th Ed., Vol. A21, VCH Verlagsgesellschaft mbH, Weinheim, 1988, p. 238–239, and H. Mark., et al., Editors, Encyclopedia of Polymer Science and Engineering, Index Volume, John Wiley & Sons, New York, 1990, p. 262–279, all of which are hereby included by reference. The N made herein by the hydrolysis of the poly(alkylene 2,6-naphthalate) may be used in normal way in these polymerizations. No special conditions are necessary due to this compound's origins.

In the Examples and Comparative Examples melting points were determined by Differential Scanning Calorimetry (DSC) at a heating rate of 20 or 25° C./min. The melting point was taken as the peak of the melting endotherm.

COMPARATIVE EXAMPLE 1

One hundred g of PEN polymer pellets (right circular cylinders approximately 0.32 cm in diameter and 0.32 cm in length) were placed in a 1780 ml, type 347 stainless steel autoclave along with 1000 g of water and 4 ml of 12 wt % toluene sulfonic acid solution in glacial acetic acid. The autoclave was sealed, and evacuated to 6.7 kPa (abs) pressure and repressurized to atmospheric pressure with nitrogen gas 3 times to remove air from the system. The sealed autoclave and its contents were then heated to 200° C. and held for 5 h at this temperature. At the end of this period, the heat was turned off, and the autoclave allowed to cool to room temperature. The resulting slurry was placed in a Waring® blender and chopped for approximately 2 min to finely disperse the particulate product. The slurry was then filtered and the recovered solid washed 2 times with a mixture of distilled water and HCl on the filter. The filtered and washed N was placed in a vacuum drying oven and dried overnight at about 120° C. and 1.3 kPa (abs) pressure. The resulting N had a slight reddish brown color, and contained about 60 ppm of antimony.

A thermotropic liquid crystal polymer was made from the recovered N by the following procedure: reactants were charged (in a nitrogen atmosphere) to a reaction vessel heated by a metal heating bath and equipped with a Vigreaux column, condenser, and a stirrer (stir speed set at 50 rpm). The reactants initially charged into the reaction vessel were 116.3 g of biphenol, 69.1 g of hydroquinone, 145.9 g of terephthalic acid, 81.4 g of N, 554.4 g of 4-hydroxybenzoic acid, and 633.9 ml of acetic anhydride. The resultant mixture was heated to reflux. The mixture was refluxed at a heating bath temperature of 170° C. for 40 min. During the next 2.75 to 3.75 h, the heating bath temperature was gradually raised to a temperature of 355° C. and by-product acetic acid was removed. Then, over the next 1 to 2 h, the pressure was gradually reduced from atmospheric to full vacuum (66 Pa to 530 Pa absolute pressure) while the stirrer speed was gradually reduced to 30 rpm. The polymerization was terminated by removing the heating bath approximately 5.5 to 8 h after the reactants were initially charged to the reaction vessel. The resulting polymer had a brown color and a melting point (as measured by DSC) of 311° C.

Example 1

Twenty g of PEN polymer pellets (right circular cylinders approximately 0.32 cm in diameter and 0.32 cm in length) were placed in a 400 ml, Hastelloy® C autoclave along with 150 ml of water and 100 ml of glacial acetic acid. The autoclave was sealed, and evacuated to 6.7 kPa (abs) pressure and repressurized to atmospheric pressure with nitrogen gas 3 times to remove air from the system. The sealed autoclave and its contents were then heated to 200° C. and held for 5 h at this temperature. At the end of this period, the heat was turned off, and the autoclave allowed to cool to room temperature. The resulting slurry was placed in a Waring® blender and chopped for approximately 2 min to finely disperse the particulate product. The slurry was then filtered and the recovered solid washed 2 times with distilled water on the filter. The filtered and washed N was placed in a vacuum drying oven and dried overnight at about 120° C. and 33.9 kPa (abs) pressure. The resulting N had a slight grayish color and contained essentially no antimony.

Example 2

Seventy-five g of PEN polymer pellets (right circular cylinders approximately 0.32 cm in diameter and 0.32 cm in length) were placed in a 1300 ml, Hastelloy® C autoclave along with 750 ml of water and 10 g of solid glycolic acid. The autoclave was sealed, and evacuated to 6.7 kPa (abs) pressure and repressurized to atmospheric pressure with nitrogen gas 3 times to remove air from the system. The sealed autoclave and its contents were then heated to 200° C. and held for 5 h at this temperature. At the end of this period, the heat was turned off, and the autoclave allowed to cool to room temperature. The resulting slurry was placed in a Waring® blender and chopped for approximately 2 min to finely disperse the particulate product. The slurry was then filtered and the recovered solid washed 2 times with distilled water on the filter. The filtered and washed N was placed in a vacuum drying oven and dried overnight at about 120° C. and 33.9 kPa (abs) pressure. The resulting N had a bright white color and contained essentially no antimony.

A thermotropic liquid crystal polymer was made from the recovered N by the following procedure: reactants were charged (in a nitrogen atmosphere) to a reaction vessel heated by a metal heating bath and equipped with a Vigreaux column, condenser, and a stirrer (stir speed set at 50 rpm). The reactants initially charged into the reaction vessel were 62.8 g of biphenol, 37.2 g of hydroquinone, 78.5 g of terephthalic acid, 43.8 g of N, 298.3 g of 4-hydroxybenzoic acid, and 341.1 ml of acetic anhydride. The resultant mixture was heated to reflux. The mixture was refluxed at a heating bath temperature of 170° C. for 40 min. During the next 2.75 to 3.75 h, the heating bath temperature was gradually raised to a temperature of 355 to 370° C. and by-product acetic acid was removed. Then, over the next 1 to 2 h, the pressure was gradually reduced from atmospheric to full vacuum (67 to 530 Pa absolute pressure) while the stirrer speed was gradually reduced to 30 rpm. The polymerization was terminated by removing the heating bath approximately 5.5 to 8 h after the reactants were initially charged to the reaction vessel. The resulting polymer had a tan color and the melting point was 329° C.

COMPARATIVE EXAMPLE 2

Twenty g of PEN polymer pellets (right circular cylinders approximately 0.32 cm in diameter and 0.32 cm in length) were placed in a 400 ml, Hastelloy® C autoclave along with 180 ml of water and 20 ml of aqueous HCl (approximately 35 wt % HCl). The autoclave was sealed, and evacuated to 6.7 kPa (abs) pressure and repressurized to atmospheric pressure with nitrogen gas 3 times to remove air from the system. The sealed autoclave and its contents were then heated to 200° C. and held for 5 h at this temperature. At the end of this period, the heat was turned off, and the autoclave allowed to cool to room temperature. The resulting slurry was poured off and examined. Both the liquid and solid components of the slurry were dark black.

COMPARATIVE EXAMPLE 3

Liquid crystal polymer was prepared from commercially purchased N according to the procedure described in Comparative Example 1. The resulting polymer had a tan color and melting point (as measured by DSC) of 329° C.

What is claimed is:

1. A process for the production of 2,6-naphthalene dicarboxylic acid, consisting essentially of, contacting, at a temperature of about 120° C. to about 300° C., a poly (alkylene 2,6-naphthalate), water, and an organic carboxylic acid, other than 2,6-naphthalene dicarboxylic acid, containing 2 to about 20 carbon atoms, and provided that said carboxylic acid is about 0.1 to about 50 volume percent of said water, or said organic carboxylic acid is about 0.05 to about 25 weight percent of said poly(alkylene 2,6-naphthalate), or said carboxylic acid is about 0.1 to about 50 volume percent of said water, and said organic carboxylic acid is about 0.05 to about 25 weight percent of said poly(alkylene 2,6-naphthalate).

2. The process as recited in claim 1 wherein said poly (alkylene 2,6-naphthalate) is a polyester only.

3. The process as recited in claim 1 wherein said poly (alkylene 2,6-naphthalate) has a repeat unit of the formula

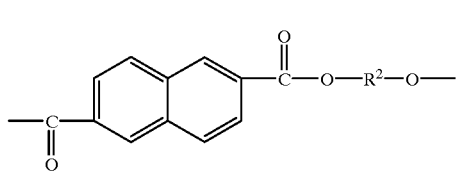

wherein $R^2$ is alkylene.

4. The process as recited in claim 3 wherein $R^2$ is —$CH_2CH_2$—.

5. The process as recited in claim 4 wherein at least some water is in the liquid phase.

6. The process as recited in claim 4 or 5 wherein said organic carboxylic acid is of the formula $R^3CO_2H$ wherein $R^3$ is alkyl containing 2 to 4 carbon atoms.

7. The process as recited in claim 4 or 5 wherein said organic carboxylic acid is acetic acid or glycolic acid.

8. The process as recited in claim 4 or 5 wherein said temperature is about 175° C. to about 250° C.

9. The process as recited in claim 8 wherein at least 3 moles of water per mole of (I) are present.

10. The process as recited in claim 8 wherein about 5 to 200 moles of water per mole of (I) are present.

11. The process as recited in claim 4 wherein about 5 to about 200 moles of water per mole of (I) are present.

12. The process as recited in claim 1 wherein said poly(alkylene 2,6-naphthalate) is poly(ethylene naphthalate), at least some water is in the liquid phase, about 5 to 200 moles of water per repeat unit of poly(ethylene naphthalate) are present, said temperature is about 175° C. to about 250° C., and said organic carboxylic acid is acetic acid or glycolic acid.

13. The process as recited in claim 1, 4 or 12 comprising the additional step of polymerizing, in a condensation polymerization, said 2,6-naphthalene dicarboxylic acid to form a polymer which contains ester linking groups, said polymerizing comprising:

(a) heating a mixture, optionally in the presence of a catalyst, of a diol with said 2,6-naphthalene dicarboxylic acid to a temperature at which the esterification occurs with the formation of polyester and byproduct water; or (b) reacting an aryl ester of said 2,6-napththalene dicarboxylic acid and one or more bisphenols, and removing by-product phenol; or (c) heating an alkanoic diester of a bisphenol, with said 2,6-napthalene dicarboxylic acid and liberating an alkanoic acid.

14. The process as recited in claim 1 wherein said organic carboxylic acid has a pKa in water at 23° C. of about 1 to about 6.

15. The process as recited in claim 1 comprising the additional steps of filtering and optionally washing said 2,6-naphthlaene dicarboxylic acid, drying said 2,6-naphthalene dicarboxylic acid, and polymerizing, in a condensation polymerization, said 2,6-napthalene dicarboxylic acid to form a polymer which contains ester linking groups, without further purification, said polymerizing comprising:

(a) heating a mixture, optionally in the presence of a catalyst, of a diol with said 2,6-naphthalene dicarboxylic acid to a temperature at which the esterification occurs with the formation of polyester and byproduct water; or (b) reacting an aryl ester of said 2,6-napththalene dicarboxylic acid and one or more bisphenols, and removing by-product phenol; or (c) heating an alkanoic diester of a bisphenol, with said 2,6-napthalene dicarboxylic acid and liberating an alkanoic acid.

16. The process as recited in claim 6 wherein about 5 to about 200 moles of water per mole of (I) are present.

* * * * *